United States Patent [19]

Hettche et al.

[11] Patent Number: 5,536,444

[45] Date of Patent: Jul. 16, 1996

[54] COMPRESSED-GAS PACKAGES USING POLYOXYETHYLENE GLYCERYL FATTY-ACID ESTERS AS SUSPENSION STABILIZERS AND VALVE LUBRICANTS

[75] Inventors: Helmut Hettche, Dietzenbach; Reinhard Muckenschnabel, Frankfurt am Main, both of Germany

[73] Assignee: ASTA Medica Aktiengesellschaft, Dresden, Germany

[21] Appl. No.: 135,356

[22] Filed: Oct. 13, 1993

[30] Foreign Application Priority Data

Jul. 8, 1993 [DE] Germany .......................... 43 22 703.1

[51] Int. Cl.[6] ................. C09K 3/30; A61K 9/00

[52] U.S. Cl. .............................. 252/305; 424/47
[58] Field of Search ................ 252/305; 424/47

[56] References Cited

FOREIGN PATENT DOCUMENTS 59-217784  12/1984  Japan .
09761      5/1993   WIPO .

*Primary Examiner*—Shean O. Wu
*Attorney, Agent, or Firm*—Cushman Darby & Cushman

[57] ABSTRACT

Aerosol compressed-gas packages for the administration of biologically active substances with novel suspension stabilizers and propellants which are not harmful to ozone.

20 Claims, No Drawings

COMPRESSED-GAS PACKAGES USING POLYOXYETHYLENE GLYCERYL FATTY-ACID ESTERS AS SUSPENSION STABILIZERS AND VALVE LUBRICANTS

The present invention relates to aerosol compressed-gas packages and more particularly to suspension stabilizers and/or valve lubricants for use therein.

BACKGROUND OF THE INVENTION

The term "aerosol compressed-gas packages" denotes compression-proof containers from which a mixture of liquefied propellant and active substance stored under pressure is released by actuation of a valve. They have been used for many years for very varied purposes. Compressed-gas packages for pharmaceuticals are described e.g. in Sucker, Fuchs und Speiser (editor), Pharmazeutische Technologie, Thieme, Stuttgart, 1991, pp. 673–688; furthermore, aerosols and compressed-gas packages are described in List, Arzneiformenlehre, Wissenschaftliche Verlagsgesellschaft, Stuttgart, 1985, pp. 8–18 and in Voigt, Lehrbuch der pharmazeutischen Technologie, VCh, Weinheim, 1987 on pages 427–436. This popular form of administration is discussed in detail by Thoma, Aerosole, Selbstverlag, Frankfurt am Main, 1979.

Aerosol compressed-gas packages are used with advantage in medicine when active substances are to be administered directly into the lung and deposited there. Their advantage relies on the fact that, when they are used, a cloud of extremely finely dispersed particles is produced which can be breathed in by the patient. As a consequence, there is a rapid effect in the area of action, i.e., the lung, which is of decisive importance for the therapy, e.g. of bronchial asthma. On the other hand, in the prevention of asthma attacks by means of prophylactically active substances, direct administration to the lung makes it possible to keep the dose low. This minimizes the occurrence of undesired side effects in comparison with administration via the gastrointestinal tract, e.g., swallowing a tablet.

Aerosol compressed-gas packages have therefore found broad acceptance in the therapy of respiratory-tract illnesses. They are simple, reliable and economical. Possible problems in the coordination of the inspiration of the patient and the release of a puff of aerosol can be avoided either by expansion chambers (spacers) inserted between the aerosol package and the mouth of the patient or by special constructions of the inhalators in which the inspiration of the patient actuates release of a puff of aerosol.

Aerosol compressed-gas packages also can be used as a nasal spray and a mouth spray for oral, lingual and buccal administration of active substances.

In the past, among others, CFC's (fluorinated, chlorinated hydrocarbons) were used as the propellant for controlled dosage aerosols. Examples of known propellants include the following fluorinated, chlorinated hydrocarbons and hydrocarbons which can be used as propellants: Pentane, n-butane, iso-butane, TG 11, TG 12, TG 21, TG 22, TG 23, TG 113, TG 114, TG 115, TG 142 b and TG C 318.

The type designation of fluorinated chlorinated hydrocarbons is derived from the following key system:
Number in unit place= number of fluorine atoms (F)
Number in decimal place minus 1= number of hydrogen atoms(H)
Number in hundred's place plus 1= number of carbon atoms (C)
Number of the valences still free= number of chlorine atoms (Cl)

Since the development of the ozone theory (postulated degradation of the stratospheric ozone by CFC's and other chlorine-containing organic compounds) a search has been conducted for liquid gases suitable as propellants which are neither combustible nor are capable of degrading ozone and, in addition, are not detrimental to health.

For some time, non-chlorinated fluorocarbons such as e.g. 1,1,1,2-tetrafluoroethane (TG 134a) and 2H-heptafluoropropane (TG 227) have been investigated. In addition to TG 134a and TG 227, TG 152a (difluoroethane, $CH_3CHF_2$) TG 143a (trifluoroethane, $CH_3CF_3$) and TG 161 (fluoroethane, $CH_3CH_2F$) could be mentioned.

However, a disadvantage of these propellants is the fact that suspension stabilizers and valve lubricants hitherto used are not sufficiently soluble in them. Thus, the use of TG 134a requires approximately 25% ethanol in order to sufficiently dissolve the sorbitan trioleate (Span®) previously used in aerosol suspensions (see EP 372,777 A 2). The following compounds can also be used by way of example: Polyvalent alcohols such as e.g. glycerol, esters such as e.g. ethyl acetate, ketones such as e.g. acetone and hydrocarbons such as e.g. hexane and heptane, pentane and also isopropanol.

Such a high concentration of alcohol is disadvantageous because the active substance in the suspension can dissolve, and there is a danger of particle growth when that occurs. If the active-substance particles grow during storage of such a suspension beyond a size of 10 μm, the aerosol valve can become clogged. In addition, the effectiveness of the aerosol can diminish, because the active-substance particles are no longer capable of reaching the lower sections of the lungs, because of their size.

There is therefore an urgent need for substances which
are physiologically acceptable
are technologically suitable for stabilizing aerosol suspensions of TG 134a or TG 227 as well as improving the function of the metering valve,
are soluble in TG 134a or TG 227 with or without using very small amounts of other physiologically acceptable solutizers,
are acceptable to the taste.

SUMMARY OF THE INVENTION

It has been surprisingly found that polyoxyethylene (7) glyceryl cocoate is a substance with the necessary properties. (trade name—Cetiol HE, manufacturer: Henkel) The structure of glyceryl cocoate (PEG-7) is given in Formula I:

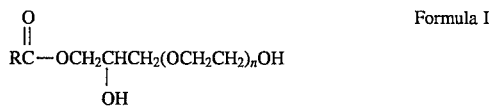

Formula I in which n has an approximate value of 7. Further suspension-stabilizing compounds exhibiting the above-mentioned properties are:

A polyoxyethylene (30) glyceryl cocoate with the abbreviation PEG-30-glyceryl cocoate (Formula II)

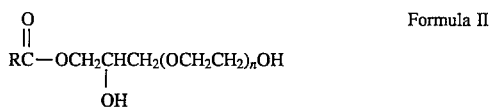

Formula II in which n has the value of approximately 30. The trade name of the compound is Varonic LI-63 and the manufacturer is Ashland Chemical Company.

In Formulas I and II,

represents the cocoate group.

The compound with the name polyoxyethylene (12)-glyceryl laurate (Formula III) can also be used:

$$CH_3(CH_2)_{10}C(=O)-OCH_2CH(OH)CH_2(OCH_2CH_2)_nOH \quad \text{Formula III}$$

where n has an average value of 12. This compound is available commercially under the name Lamacit GML-12, manufacturer: Chemische Fabrik Grunau.

Polyoxyethylene (20)—glyceryl laurate (Formula IV) can also be used as suspension stabilizer:

$$CH_3(CH_2)_{10}C(=O)-OCH_2CH(OH)CH_2(OCH_2CH_2)_nOH \quad \text{Formula IV}$$

where n has an average value of 20. It is commercially available under the name Lamacit GML-20 from the Chemische Fabrik Grunau or under the name Tagat L2 from the Goldschmidt AG. Tagat L2 has an HLB value of 15.7± 1 [HLB indicates "hydrophilic-lipophilic balance"]. The following can also be used: Polyoxyethylene (30)—glyceryl laurate (Formula V)

$$CH_3(CH_2)_{10}C(=O)-OCH_2CH(OH)CH_2(OCH_2CH_2)_nOH \quad \text{Formula V}$$

where n has an average value of 30. It is available commercially under the trade name Tagat L from the Goldschmidt company. Tagat L has an HLB value of 17.0±1.

Polyoxyethylene (25)—glyceryl oleate (Formula VI) can also be used:

$$\begin{array}{l} CH(CH_2)_7CH_3 \\ \parallel \\ CH(CH_2)_7C(=O)-OCH_2CHOH \\ \phantom{CH(CH_2)_7C(=O)-O}CH_2(OCH_2CH_2)_nOH \end{array} \quad \text{Formula VI}$$

where n has an average value of 25. The compound is available commercially under the name Lamacit GMO-25 from the Chemische Fabrik Grunau. Lamacit GMO-25 has an HLB value of 16.2±1.

The following can also be used: Polyoxyethylene (15) glyceryl ricinoleate (Formula VII):

$$\begin{array}{l} OH \\ | \\ CHCH_2CH(CH_2)_5CH_3 \\ \parallel \\ CH(CH_2)_7C(=O)-OCH_2CHOH \\ \phantom{CH(CH_2)_7C(=O)-O}CH_2(OCH_2CH_2)_nOH \end{array} \quad \text{Formula VII}$$

where n has an average value of 15. This compound is commercially available under the name Tagat R1, manufacturer: Goldschmidt AG. Tagat R1 has an HLB value of 14.0±1.

Furthermore, a polyoxyethylene (20)—glyceryl ricinoleate according to Formula VIII can be used $$\begin{array}{l} OH \\ | \\ CHCH_2CH(CH_2)_5CH_3 \\ \parallel \\ CH(CH_2)_7C(=O)-OCH_2CHOH \\ \phantom{CH(CH_2)_7C(=O)-O}CH_2(OCH_2CH_2)_nOH \end{array} \quad \text{Formula VIII}$$

in which n has a value of 20. The compound is commercially available under the name Lamacit ER, manufacturer: Chemische Fabrik Grunau.

A polyoxyethylene (5)—glyceryl stearate (PEG-5) (Formula IX) can also be used:

$$CH_3(CH_2)_{16}C(=O)-OCH_2CH(OH)CH_2(OCH_2CH_2)_nOH \quad \text{Formula IX}$$

in which the value of n is approximately 5.

PEG-5 is commercially available under the name POEM-S-105.

Polyoxyethylene (10)—glyceryl stearate (Formula X)

$$CH_3(CH_2)_{16}C(=O)-OCH_2CH(OH)CH_2(OCH_2CH_2)_nOH \quad \text{Formula X}$$

can also be used where n has an average value of 10.

Polyoxyethylene (20)—glyceryl stearate (Formula XI)

$$CH_3(CH_2)_{16}C(=O)-OCH_2CH(OH)CH_2(OCH_2CH_2)_nOH \quad \text{Formula XI}$$

can also be used, in which n has a value of 20. It is commercially available under the name Cutina E-24 from Henkel and under the name Tagat S2 from Goldschmidt AG. Tagat S2 has an HLB value of 15.0± 1.

Polyoxyethylene (30)—glyceryl stearate (Formula XII)

$$CH_3(CH_2)_{16}C(=O)-OCH_2CH(OH)CH_2(OCH_2CH_2)_nOH \quad \text{Formula XII}$$

can also be used, in which n has a value of approximately 30. It is commercially available under the name Tagat S from the Goldschmidt AG company. Tagat S has an HLB value of 16.4±1.

Polyoxyethylene (120)—glyceryl stearate (Formula XIII):

$$CH_3(CH_2)_{16}C(=O)-OCH_2CH(OH)CH_2(OCH_2CH_2)_nOH \quad \text{Formula XIII}$$

can also be used, in which n has an average value of 120. It is commercially available under the name Drewmulse 1128, manufacturer Drew Chemical Corporation.

Polyoxyethylene (28)—glyceryl tallowate according to Formula XIV can also be used:

$$R^1C(=O)-OCH_2CH(OH)CH_2(OCH_2CH_2)_nOH \quad \text{Formula XIV}$$

In this formula, $$R^1-\overset{O}{\underset{\|}{C}}-$$

refers to the residue of tall oil fatty acids and n has an average value of 28. It is commercially available under the name Varonic LI 2 from the Ashland Chemical Company.

Polyoxyethylene glyceryl fatty-acid esters according to formulas I to XIV are
  physiologically acceptable
  technologically suitable for stabilizing aerosol suspensions of TG 134a or TG 227 as well as improving the function of the metering valve,
  soluble in TG 134a or TG 227 when less than 1–2% ethanol or of comparable alcohols is present,
  and acceptable to the taste.

The dissolving capacity of a mixture of TG 134a or TG 227 with 1–2% ethanol for the conventional active ingredients is so low that it does not contribute to possible crystal growth of the active ingredient. The suspension stabilizers previously used in commercial preparations had an HLB value of below 5 (e.g. Span 85: HLB= 1.8) and are thus in the category of water in oil emulsifiers (Voigt, Lehrbuch der pharmazeutischen Technologie, Weinheim, 1987, p. 332).

It is therefore surprising that substances such as compounds according to formulas I–XIV with an HLB value of >10 are suitable for this purpose.

The HLB value is explained in Rompps Chemie-Lexikon, Stuttgart, 1973, vol. 3, pp. 1478–1479.

The amount of compounds of formulas I to XIV used relative to an amount of active substance used is e.g. between 0.1 and 8000, especially between 5 and 4000 and specially preferably between 15 and 2500.

The following can be used as active substances:

Analgesics, anti-allergic agents, antibiotics, anticholinergic drugs, antihistamines, substances with an anti-inflammatory action, antitussives, bronchodilators, diuretics, enzymes, substances active in the cardiovascular system, hormones, proteins and peptides. Examples of analgesics are codeine, diamorphine, dihydromorphine, ergotamine, fentanyl, morphine; examples of anti-allergic agents are cromoglycic acid, nedocromil; examples of antibiotics are cephalosporins, fusafungin, neomycin, penicillins, pentamidine, streptomycin, sulfonamides, tetracyclines; examples of anticholinergic drugs are atropine, atropine methonitrate, ipratropium bromide, oxytropium bromide, trospium chloride; examples of antihistamines are azelastine, flezelastine, methapyrilene; examples of substances with anti-inflammatory action are beclomethasone, budesonide, dexamethasone, flunisolide, fluticasone, tipredane, triamcinolone; examples of antitussives are narcotin, noscapine; examples of bronchodilators are bambuterol, bitolterol, carbuterol, clenbuterol, ephedrine, epinephrine, formoterol, fenoterol, hexoprenaline, ibuterol, isoprenaline, isoproterenol, metaproterenol, orciprenaline, phenylephrine, phenylpropanolamine, pirbuterol, procaterol, reproterol, rimiterol, salbutamol, salmeterol, sulfonterol, terbutaline, tolobuterol; examples of diuretics are amiloride, furosemide; an example of enzymes is trypsin; examples of substances active in the cardiovascular system are diltiazem and nitroglycerin; examples of hormones are cortisone, hydrocortisone, prednisolone; examples of proteins and peptides are cyclosporins, cetrorelix, glucagon, insulin. Further active substances which can be used are adrenochrome, colchicine, heparin, scopolamine.

Mixtures of the substances cited above can also be used.

The active substances cited by way of example can be used as free bases or acids or as pharmaceutically acceptable salts. For example, physiologically acceptable alkaline-earth metals or alkaline metals or amines as well as e.g. acetate, benzene sulfonate, benzoate, hydrogen carbonate, hydrogen tartrate, bromide, chloride, iodide, carbonate, citrate, fumarate, malate, maleate, gluconate, lactate, pamoate, hydroxynaphtoate and sulfate can be used as counter-ions. Esters can also be used, e.g. acetate, acetonide, propionate, dipropionate, valerate. The amount of substances according to Formulas I–XIV relative to the total mixture, composed of active ingredients, propellant or propellant mixtures and optional auxiliary agents, is e.g. 0.01% by weight—5% by weight, especially 0.2% by weight —2.5% by weight and especially preferably 0.75% by weight —1.5% by weight.

The addition of cosolvents is possible, e.g. aliphatic alcohols with 2 to 6 carbon atoms or their esters or ketones or polyols. Examples are ethanol, isopropanol, propylene glycol, acetone, ethyl acetate, n-propanol, preferably ethanol and isopropanol.

The amount of ethanol or isopropanol relative to the total mixture is between 0% by weight and 10% by weight, especially 0.1% by weight to 2% by weight and especially preferably 0.2% by weight to 1% by weight.

The addition of further surface-active substances such as is mentioned e.g. in EP 0 372 777 is of course possible.

The suspending of the active substances can be carried out either under normal air pressure, in which instance the suspension medium must be cooled down to low temperatures (e.g. –35° C. to –55° C.) or within a pressurized container, in which instance the operation can be performed at normal temperatures (room temperature 15 ° C. to 25 ° C.).

The suspension is homogenized and subsequently dispensed into pressure cans, which are closed with a metering valve or are subsequently closed.

DETAILED DESCRIPTION OF PREFERRED EMBODIMENTS

The invention is illustrated by the following examples.

EXAMPLE 1

1000 g 2H-heptafluoropropane (= propellant [aerosol propellant] 227) are cooled to a temperature of approximately –55° C. and combined with agitation with a solution of 11.7 g polyoxyethylene-20-glyceryl monolaurate (trade name: Tagat L2, Goldschmidt AG) in 11.7 g absolute ethanol. Then, 16.8 g micronized cromolyn sodium and 8.4 g micronized reproterol hydrochloride as well as 0.9 g micronized saccharin sodium and 6.75 g peppermint oil are added and the suspension produced is intensively homogenized. The suspension is combined with cooled propellant 227 to 1170.0 g with further agitation and cooling and then dispensed into metal cans which are closed with metering valves which release 50 µl of suspension with each stroke. Thus, 1 mg cromolyn sodium and 0.5 mg reproterol hydrochloride are released per stroke.

EXAMPLE 2

The same procedure is followed as in Example 1; however, instead of 16.8 g micronized cromolyn sodium and 8.4 g micronized reproterol hydrochloride, 16.8 g micronized D-18024 are used. Thus, 1 mg D-18024 is released per stroke. D-18024 has the following structural formula:

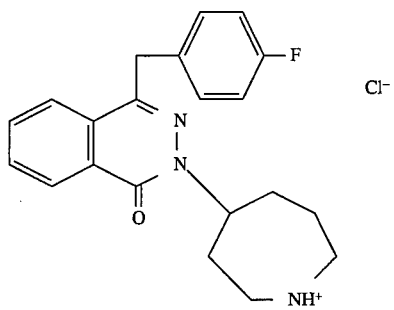

D-18024 carries the INN flezelastine hydrochloride.

EXAMPLE 3

The same procedure is used as in Example 1; however, instead of 16.8 g micronized cromolyn sodium 8.4 g micronized reproterol hydrochloride, 0.9 g micronized saccharin sodium and 6.75 g peppermint oil, 4.2 g micronized budesonide are used. Each stroke delivers 0.25 mg budesonide.

What is claimed is:

1. In an aerosol compressed-gas package for administering non-aqueous preparations of biologically active substances, said package containing a compressed propellant, a biologically active substance and a suspension stabilizer and/or valve lubricant;

the improvement in which the suspension stabilizer and/or valve lubricant is selected from the group consisting of the compound of Formula I, in which n is 7,

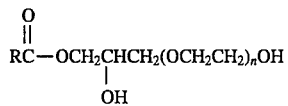
Formula I the compound of Formula II, in which n is 30,

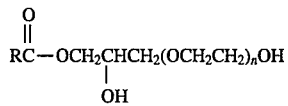
Formula II the compound of Formula III, in which n has an average value of 12,

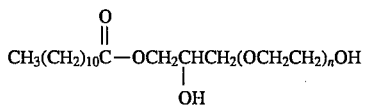
Formula III the compound of Formula IV, in which n has an average value of 20,

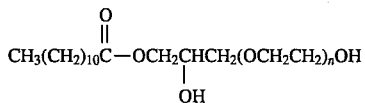
Formula IV the compound of Formula V, in which n has an average value of 30,

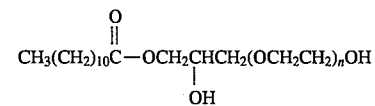
Formula V the compound of Formula VI, in which n has an average value of 25,

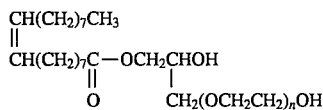
Formula VI the compound of Formula VII, in which n has an average value of 15,

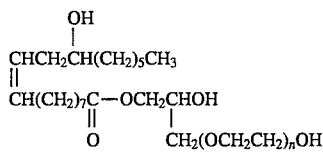
Formula VII the compound of Formula VIII, in which n is 20,

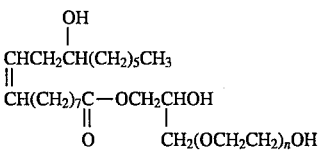
Formula VIII the compound of Formula IX, in which n is 5,

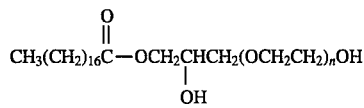
Formula IX the compound of Formula X, in which n is 10,

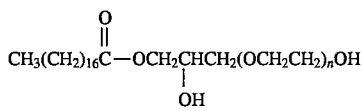
Formula X the compound of Formula XI, in which n is 20,

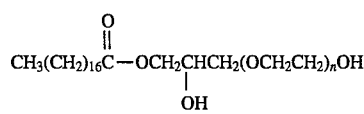
Formula XI the compound of Formula XII, in which n is 30,

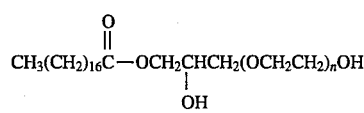
Formula XII the compound of Formula XIII, in which n has an average value of 120,

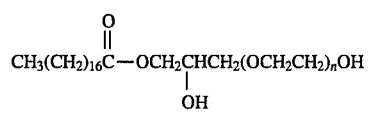
Formula XIII and the compound of Formula XIV, in which n has an average value of 28,

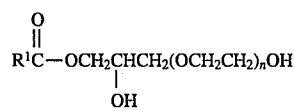
Formula XIV

2. An aerosol compressed gas package as set forth in claim 1 in which the suspension stabilizer and/or valve lubricant is the compound of Formula I.

3. An aerosol compressed gas package as set forth in claim 1 in which the suspension stabilizer and/or valve lubricant is the compound of Formula II.

4. An aerosol compressed gas package as set forth in claim 1 in which the suspension stabilizer and/or valve lubricant is the compound of Formula III.

5. An aerosol compressed gas package as set forth in claim 1 in which the suspension stabilizer and/or valve lubricant is the compound of Formula IV.

6. An aerosol compressed gas package as set forth in claim 1 in which the suspension stabilizer and/or valve lubricant is the compound of Formula V.

7. An aerosol compressed gas package as set forth in claim 1 in which the suspension stabilizer and/or valve lubricant is the compound of Formula VI.

8. An aerosol compressed gas package as set forth in claim 1 in which the suspension stabilizer and/or valve lubricant is the compound of Formula VII.

9. An aerosol compressed gas package as set forth in claim 1 in which the suspension stabilizer and/or valve lubricant is the compound of Formula VIII.

10. An aerosol compressed gas package as set forth in claim 1 in which the suspension stabilizer and/or valve lubricant is the compound of Formula IX.

11. An aerosol compressed gas package as set forth in claim 1 in which the suspension stabilizer and/or valve lubricant is the compound of Formula X.

12. An aerosol compressed gas package as set forth in claim 1 in which the suspension stabilizer and/or valve lubricant is the compound of Formula XI.

13. An aerosol compressed gas package as set forth in claim 1 in which the suspension stabilizer and/or valve lubricant is the compound of Formula XII.

14. An aerosol compressed gas package as set forth in claim 1 in which the suspension stabilizer and/or valve lubricant is the compound of Formula XIII.

15. An aerosol compressed gas package as set forth in claim 1 in which the suspension stabilizer and/or valve lubricant is the compound of Formula XIV.

16. An aerosol compressed-gas package according to claim 1 in which the proportion of suspension stabilizer and/or valve lubricant, relative to the total weight of the mixture, is between 0.01 and 5% by weight.

17. An aerosol compressed-gas package according to claim 1 in which the proportion of suspension stabilizer and/or valve lubricant, relative to the total weight of the mixture, is between 0.2 and 2.5% by weight.

18. An aerosol compressed-gas package according to claim 1 in which the proportion of suspension stabilizer and/or valve lubricant, relative to the total weight of the mixture, is between 0.75 and 1.5% by weight.

19. An aerosol compressed-gas package according to claim 1 in which the propellant is at least one member of the group consisting of 2H-heptafluoropropane and 1, 1, 1, 2-tetrafluoroethane.

20. An aerosol compressed-gas package as set forth in claim 1 in which the biologically active substance is a flezelastine salt.

* * * * *